United States Patent
Yokajty et al.

[11] Patent Number: 5,955,740
[45] Date of Patent: Sep. 21, 1999

[54] INSPECTION METHOD AND APPARATUS FOR DETERMINING THE SIDE-UP ORIENTATION OF AN OBJECT RESTING ON A FLAT SURFACE

[75] Inventors: Joseph E. Yokajty, Webster; Thomas W. Palone, Rochester, both of N.Y.

[73] Assignee: Eastman Kodak Company, Rochester, N.Y.

[21] Appl. No.: 08/991,491

[22] Filed: Dec. 16, 1997

[51] Int. Cl.[6] ................................................. G01N 21/84
[52] U.S. Cl. ........................... 250/559.08; 250/223 R; 250/223 B
[58] Field of Search .......................... 250/559.08, 223 R, 250/223 B, 202; 356/239.4, 239.8, 240.1; 198/394

[56] References Cited

U.S. PATENT DOCUMENTS

| | | | |
|---|---|---|---|
| 1,997,712 | 4/1935 | Bauer | 356/379 |
| 3,484,615 | 12/1969 | Noro et al. | 356/379 |
| 3,708,679 | 1/1973 | Stock et al. | 250/223 R |
| 3,778,618 | 12/1973 | Laskowski | 250/223 R |
| 3,837,732 | 9/1974 | Bauer | 359/798 |
| 4,063,823 | 12/1977 | Grat | 356/427 |
| 4,070,575 | 1/1978 | Park et al. | 250/223 R |
| 4,147,433 | 4/1979 | Drinkuth | 356/390 |
| 4,147,930 | 4/1979 | Browne et al. | 250/223 R |
| 4,171,161 | 10/1979 | Jung | 356/383 |
| 4,390,278 | 6/1983 | Inoue | 356/392 |
| 4,459,027 | 7/1984 | Kafri et al. | 356/376 |
| 4,497,576 | 2/1985 | Caussignac et al. | 356/335 |
| 4,509,075 | 4/1985 | Simms et al. | 348/129 |
| 4,678,920 | 7/1987 | Iadipaolo et al. | 250/559.05 |
| 4,786,801 | 11/1988 | Shay | 250/223 B |
| 4,805,124 | 2/1989 | Krufka | 702/155 |
| 4,959,537 | 9/1990 | Kimoto et al. | 250/223 B |
| 5,114,230 | 5/1992 | Pryor | 356/372 |
| 5,280,170 | 1/1994 | Baldwin | 250/223 B |
| 5,314,055 | 5/1994 | Gordon | 198/395 |
| 5,392,360 | 2/1995 | Weindelmayer et al. | 382/151 |
| 5,402,193 | 3/1995 | Choate | 353/80 |
| 5,405,015 | 4/1995 | Bhatia et al. | 209/524 |
| 5,440,385 | 8/1995 | Fein et al. | 356/239.1 |

Primary Examiner—Edward P. Westin
Assistant Examiner—Thanh X. Luu
Attorney, Agent, or Firm—Mark G. Bocchetti

[57] ABSTRACT

A method and apparatus which can reliably inspect three dimensional objects resting on a surface such that part type, part location, side-up orientation, and orientation about a vertical axis can be determined with a single camera. The object to be inspected is supported on a support member which may be a conveyor. The support member possesses two specific optical characteristics. First, the support member must permit direct viewing therethrough of the object supported thereon without any significant loss of clarity. The support member must also be capable of diffuse reflection of a portion of the light incident thereon. A camera is positioned below the support member and a light source is positioned above the support member to back-light the object for the camera. That portion of the light diffusely reflected off the support member serves to illuminate any downward-facing surfaces of the object which are not in contact with the support member. Surfaces of the object which are in contact with the support member are darker than downward-facing surfaces of the object which are not in contact with the support member. A computer evaluates the image.

18 Claims, 2 Drawing Sheets

INSPECTION METHOD AND APPARATUS FOR DETERMINING THE SIDE-UP ORIENTATION OF AN OBJECT RESTING ON A FLAT SURFACE

FIELD OF THE INVENTION

The present invention relates generally to the inspection of three dimensional objects resting on a surface and, more particularly, to the determination of the side-up orientation and location of objects on a surface.

BACKGROUND OF THE INVENTION

Parts feeders used in the manufacturing industry are well known. Typically, such parts feeders comprise bowls or hoppers containing a bulk source of parts. The parts are delivered to a conveying apparatus which is intended to aid in separating the parts. The use of vision-based flexible parts feeders is a relatively new phenomenon in the manufacturing industry which is gaining credibility. With the use of such vision-based parts feeders, companies are able to make their manufacturing systems more flexible in order to cost effectively automate the production of smaller volume products. Typically, in operation, such parts feeders deliver bulk parts from a source to a transport surface for inspection and subsequent picking therefrom by a robot. Preferably, a single camera is used to inspect the separated parts on the transport surface. The inspection is primarily used to identify which parts may be successfully grasped by the robot as well as the location of each identified "pickable" part.

In general, the "flexibility" of a vision-based flexible parts feeder is closely related to the ability of the lighting system to illuminate the widest range of part types in a way that permits successful object recognition by the camera understanding that the different part types are randomly oriented. One flexible parts feeder known in the prior art is the Flexfeeder 250 manufactured by Adept Technologies of San Jose, Calif. This particular feeder comprises a translucent belt on which parts are placed for inspection by a downward-looking camera. Light is projected from the underside of the translucent belt which is more commonly known as back-lighting. This lighting method is relatively common and is a very robust means to illuminate a wide variety of parts including parts which have very little color contrast with the belt. However, in many cases where parts possess a profile symmetry, no distinction can be made by the camera as to whether or not the part is right side up or upside down since the image seen by the camera is only its silhouette or perimetric shape. One example of a such a part with perimetric symmetry is a small gear with an axially extending hub on one side. Due to lighting conditions, the back-lighting of the Flexfeeder 250 does not permit a distinction to be made between such a gear with the axially extending hub facing upward and such a gear with the axially extending hub facing downward.

Another flexible parts feeder known in the art is the programmable reconfigurable parts feeder manufactured by Intelligent Automation Systems, Inc., of Cambridge, Mass. This particular parts feeder also utilizes a translucent belt on which parts are placed in single file for inspection by a downward-looking camera. In addition, a mirror is located next to the part inspection location and tilted at 45 degrees. This allows a "second view" without the need for adding another camera. Depending on the specific part geometry, this may or may not provide the information needed to determine actual part orientation because the shape of the "second view" of the part may vary with orientation of the part about its vertical axis.

U.S. Pat. No. 5,280,170 to Baldwin teaches an inspection machine wherein a vertically standing container is transported to an inspection location on a transparent conveyor. There is a diffuser plate located beneath the transparent container. A beam of collimated light is directed vertically downward toward the diffuser plate and a two-dimensional camera actually views the shadow of the container cast onto the diffuser plate and the image is processed to evaluate circumference of the container. Thus, Baldwin's machine has the capability of only viewing the silhouette. Orientation of the vertically standing container is known prior to inspection.

The prior art fails to teach a method or apparatus wherein parts can be visually inspected by a single camera such that randomly oriented parts (there may be several different types of parts present) can be identified and further, the side-up orientation of such parts can be determined.

SUMMARY OF THE INVENTION

It is, therefore, an object of the present invention to provide a method and apparatus which can reliably inspect three dimensional objects resting on a surface such that part type, part location, side-up orientation, and orientation about a vertical axis can be determined with a single camera.

Another object of the present invention is to provide a method and apparatus for illuminating three dimensional objects supported on a surface in a way which enables inspection with a single CCD camera or other image capturing means.

Briefly stated, the foregoing and numerous other features, objects and advantages of the present invention will become readily apparent upon a review of the detailed description, claims and drawings provided herein. These features, objects and advantages are accomplished by placing the object to be inspected on a support member which possesses two specific optical characteristics. First, the support member must permit direct viewing therethrough of the object supported thereon without any significant loss of clarity. It should be understood that a sharp image of the objects perimeter permits the most reliable object recognition process by a vision system. Thus, to permit this type of viewing through the support member, the support member must be optically clear or posses a certain porosity through which viewing can take place. The support member must also be capable of reflection (preferably diffuse reflection) of a portion of the light incident thereon. A light source is positioned directly above that section of the support member on which the object supported to thereby provide a back-lit, white background to view the object against. A camera is positioned below the support member to view the objects through the support member. The optically clear aspect of the support member permits viewing of the object through the support member. The diffusely reflective aspect of the support member serves to illuminate those downward facing surfaces of the objects supported on the support member which are not actually in contact with the support member. Thus, the image viewed through the support member will be of varying contrasts. Those portions of the object in contact with the support member will appear darker than the downwardly facing surfaces which are elevated away from the support member. In such manner, the captured image can be used by a computer to determine the side-up orientation of the objects. The sharp image of the object's perimeter, of course, further allows the computer to determine the type of object, the location of the object, and orientation of the object about a vertical axis thereof. Thus, a variety of different objects may be placed on a support member which acts as a conveyor and the images captured thereof by the camera can be transmitted to a computer to make the above-stated determinations. The support member may be conveyor belt type device, a vibratory conveyor, a slip-stick conveyor, or the like.

DETAILED DESCRIPTION OF THE INVENTION

Figures 1, 2, 3:
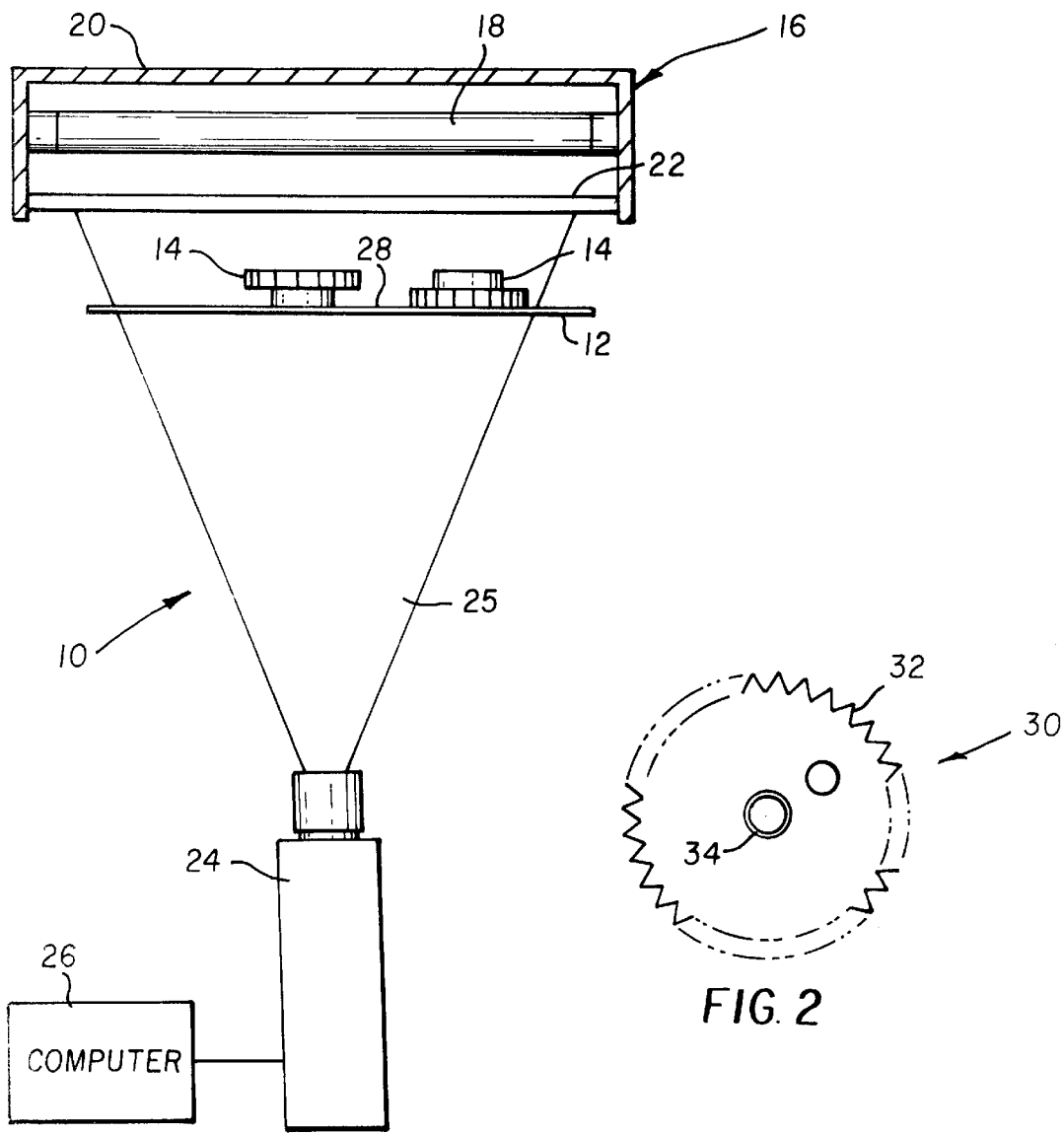
FIG. 1 is a side elevation schematic of the apparatus of the present invention.
FIG. 2 is a top plan view of an exemplary object to be inspected with the apparatus of the present invention.
FIG. 3 is a side elevational view of an exemplary object to be inspected with the apparatus of the present invention.

Turning first to FIG. 1, there is shown the apparatus 10 of the present invention. The apparatus 10 includes a support member 12 such as a conveyor belt driven and supported by means not shown for supporting objects or parts 14 to be inspected thereon. Mounted directly over and preferably in close proximity to objects 14 is a light source 16. Light source 16 is preferably a light table-type light comprising a bulb 18, an enclosure 20 and a light diffusing member 22. Positioned below support member 12 for viewing and inspection of objects 14 is image capture or camera means 24. Image capture means 24 is a camera device such as a CCD image sensor array, a CMOS image sensor array, or a photo diode array. In addition, image capture means 24 may use vidicon tube technology. Depending on the type of image capture means 24 used, light source 16 may also include filter media. The downward facing area of light source 16 must be at least as large as the field of view 25 of camera 24 at support member 12, and preferably larger. Images captured by camera 24 are evaluated by computer 26 which compares the captured images with preprogrammed images of the potential side-up orientation of the various objects 14 which might be supported on support member 12.

Support member 12 must possess two specific and different optical characteristics to permit the creation of the desired images when the support member 12 and the objects 14 supported thereon are illuminated by light source 16. Support member 12 must be, to a large extent, optically clear such that viewing of the objects 14 can be accomplished by camera 24 therethrough. It is believed that the optically clear portion of the support member 12 should be in the range of from about twenty percent to about seventy percent of the area of support member 12. The actual range may widen or narrow depending on the characteristics of the particular components (e.g., camera, light source) used and the size and structure of the objects 14 being inspected. In addition, support member 12 must also serve as a diffuser which diffusely reflects and/or diffusely transmits incident light. That is, support member 12 must be able to diffusely reflect a portion of the light produced by light source 16 in order to illuminate those downward facing surfaces of objects 14 which are not in contact with the top surface 28 of support member 12. Thus, support member 12 may take on a variety of structures. Support member 12 may be a piece of fine mesh silk-screen with the openings therethrough permitting direct viewing of objects 14 by camera 24. The individual threads of the fine mesh silk-screen would serve as the diffuse reflector portion of the support member 12. Successful testing of the present invention was performed using a fine mesh silk-screen for support member 12 having a thread diameter of about 3 mils and pores or openings therethrough which comprised about 35 percent of the surface area of support member 12. A thin clear web with an optical micro-replication pattern on the top surface thereof could also be used for support member 12. The optical micro-replication pattern would impart the diffuse reflector characteristics of the support member 12 with the remaining clear portions of the web permitting direct viewing of objects 14 therethrough. Another potential structure for support member 12 is a clear glass or plastic or other optically clear material with a finely etched pattern on the top surface. The finely etched pattern would give such a support member 12 the diffuse reflector characteristic necessary and the remaining clear portion of the glass would permit direct viewing of the objects 14 supported thereon. Support member 12 may take the form of glass or plastic with selective laser marking of the surface thereof to create the desired light diffusing property. Similarly, support member 12 may be a clear plastic film a fine pitch pattern printed thereon with a translucent ink, or a clear plastic or other optically clear material which has a partially textured top surface to achieve the desired light diffusing characteristic. As used herein, the term "translucent" is intended to mean transmitting and diffusing light so that objects beyond cannot be seen clearly. It should be understood that the very small optical features of support member 12 which cause the diffuse reflection characteristic must be small enough to be undetectable by the camera (normally due to camera resolution limitations). A blur filter may be used in some situations to prevent detectability by the camera of those small optical features.

Light source 16 should be in close proximity to objects 14 and support member 12 to achieve the lowest incident angle of light with respect to the support member 12. This lowest incident angle lighting maximizes the amount of light reflecting off of the top surface 28 of support member 12 and on to the downward-facing surfaces of objects 14. As a result, surfaces of objects 14 which are in contact with top surface 28 appear darker and can, thus, be identified by camera 24 to enable computer 26 to distinguish the side-up orientation of the object 14 since the contact area differs depending on the side-up orientation.

Figure 4:
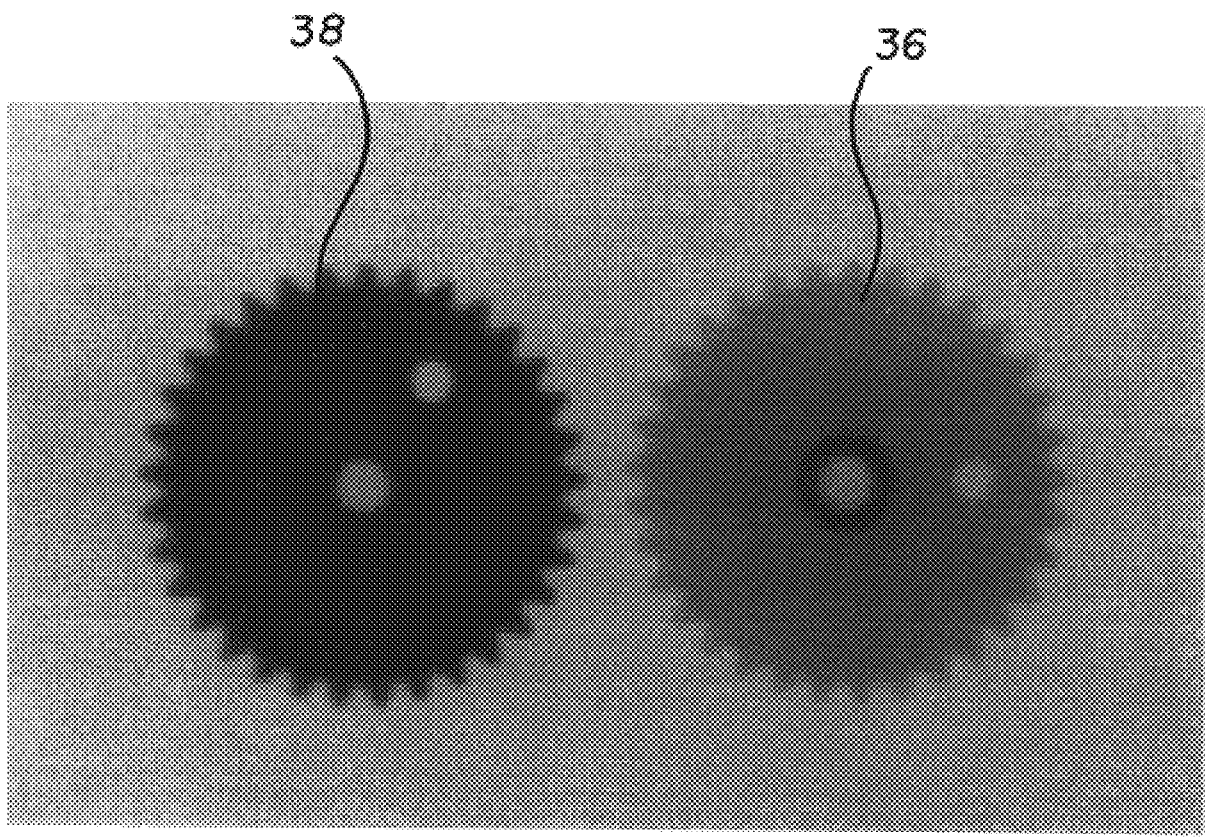
FIG. 4 is a representation of the image seen by the camera of two identical objects with opposite side-up orientations.

Looking next at FIGS. 2 and 3, there is depicted a gear 30 which is used herein as an exemplary object 14. Gear 30 includes a gear portion 32 and an axially extending hub portion 34 extending from one side of gear portion 32. FIG. 4 shows the resulting image of two gears 30 supported on support member 12 as captured by camera 24. The gears are identical with the exception that image 36 shows a gear where the gear side is supported against the top surface 28 of support member 12. Image 38 shows a gear where the hub portion 34 is supported on the top surface 28 of support member 12. In both case, the computer 24 identifies the type of part by its perimetric outline. The side-up orientation is determined by those portions of the images 36, 38 which are darker. The darker regions indicate those portions which are in contact with top surface 28 and are, therefore, not illuminated by that portion of the light from light source 16 which is diffusely reflected by support member 12. Those downward-facing surfaces of gear 30 which are not in contact with top surface 28 are, thus, lighter than those surfaces which are in contact with top surface 28.

The lighting of the present invention results in the ability to reliably "see" different images that are not only a function of the inspected object's shape but also the shape of the contact area between the object 14 and the support member 12. The image of a specific object 14 in a specific side-up orientation is not affected by the object's orientation about a vertical axis or the object's location within the camera field of view due to the uniformity of the lighting across the entire field of view. As such, this lighting method may be used to achieve a universal lighting technique for use with vision-based flexible parts feeders.

Those skilled in the art will recognize that in an alternative embodiment of the present invention, depending on the size and shape of objects being inspected a thin, clear support member can be used to convey the objects with a fixed silk-screen member of the like positioned immediately beneath the thin, clear support member. The term "support member" as used herein is intended to include such a two component arrangement.

From the foregoing, it will be seen that this invention is one well adapted to attain all of the ends and objects hereinabove set forth together with other advantages which are apparent and which are inherent to the invention.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth and shown in the accompanying drawings is to be interpreted as illustrative and not in a limiting sense.

What is claimed is:

1. An apparatus for inspecting an object supported on a flat surface to determine a type of object and a side-up orientation of the object, said apparatus comprising:

(a) a support member having a top surface on which the object is supported, said support member having an optically clear portion and a diffusely reflective portion;

(b) a light source positioned above said support member proximate to the object; and (c) image capturing means positioned below said support member for capturing an image of the object through said support member.

2. An apparatus as recited in claim 1 further comprising: a computer for evaluating said image.

3. An apparatus as recited in claim 1 further comprising: a computer for comparing said image to a series of pre-programmed images of possible objects and orientations to determine the type of object and the side-up orientation of the object.

4. An apparatus as recited in claim 1 wherein: said support member is a silk-screen.

5. An apparatus as recited in claim 1 wherein: said support member is a clear plastic with a fine, light diffusing pattern imparted thereto.

6. An apparatus as recited in claim 1 wherein: said support member is an optically clear material with a fine, light diffusing pattern imparted thereto.

7. An apparatus as recited in claim 1 wherein: said image capturing means is a camera.

8. An apparatus as recited in claim 1 wherein: said image capturing means is a CMOS image sensor array.

9. An apparatus as recited in claim 1 wherein: said image capturing means is a CCD camera.

10. An apparatus as recited in claim 1 wherein: said image capturing means is a photo diode array.

11. An apparatus as recited in claim 1 wherein: said image capturing means is vidicon camera.

12. An apparatus as recited in claim 1 wherein: said support member is a clear plastic with a fine pitch pattern printed thereon with translucent ink.

13. An apparatus as recited in claim 1 wherein: said support member is a clear plastic with a fine pitch pattern etched therein.

14. An apparatus as recited in claim 1 wherein: said support member is a partially textured, clear plastic.

15. A method for inspecting an object to determine a type of object and a side-up orientation of the object, said method comprising the steps of:

(a) supporting the object on a support member;

(b) directing light from a source in above the object at the object and the support member;

(c) diffusely reflecting a portion of the light of said directing step with the support member;

(d) passing a remainder of the light of said directing step which is incident on the support member through the support member unaffected; and (e) capturing an image of the object from beneath the support member.

16. A method as recited in claim 15 further comprising the step of: evaluating said image.

17. A method as recited in claim 15 further comprising the step of: comparing said image to a series of pre-programmed images of possible objects and orientations to determine the type of object and the side-up orientation of the object.

18. A method as recited in claim 15 further comprising the step of: illuminating any downwardly facing surfaces of the object with the portion of light of said diffusely reflecting step.

* * * * *